United States Patent [19]

Buell

[11] 4,081,301
[45] Mar. 28, 1978

[54] METHOD AND APPARATUS FOR CONTINUOUSLY ATTACHING DISCRETE, STRETCHED ELASTIC STRANDS TO PREDETERMINED ISOLATED PORTIONS OF DISPOSABLE ABOSRBENT PRODUCTS

[75] Inventor: Kenneth B. Buell, Forest Park, Ohio

[73] Assignee: The Procter & Gamble Company, Cincinnati, Ohio

[21] Appl. No.: 627,405

[22] Filed: Oct. 30, 1975

[51] Int. Cl.$^2$ .................... A61F 13/16; B32B 31/08
[52] U.S. Cl. ..................... 156/164; 2/401;
128/287; 156/201; 156/202; 156/216; 156/229;
156/269; 156/285; 156/290; 156/291; 156/301;
156/522; 156/523; 156/548; 156/464; 156/495;
156/549
[58] Field of Search ............. 156/160, 201, 202, 204,
156/213, 216, 222, 227, 229, 291, 295, 301, 464,
495, 522, 285; 128/284, 287; 2/400, 401;
156/269, 164, 523, 548, 549, 290, 582, 583

[56] References Cited
U.S. PATENT DOCUMENTS

| | | | |
|---|---|---|---|
| 3,463,690 | 8/1969 | Converse et al. | 156/291 |
| 3,488,778 | 1/1970 | Goujon et al. | 128/284 |
| 3,528,878 | 9/1970 | Lubowitz et al. | 156/331 |
| 3,560,292 | 2/1971 | Butter | 156/229 |
| 3,616,770 | 11/1971 | Blyther et al. | 112/121.26 |
| 3,663,962 | 5/1972 | Burger | 2/224 A |
| 3,694,815 | 10/1972 | Burger | 2/224 A |
| 3,730,798 | 5/1973 | Franz | 156/291 |
| 3,746,592 | 7/1973 | Nystrand et al. | 156/213 |
| 3,828,367 | 8/1974 | Burgeois | 2/224 A |
| 3,881,488 | 5/1975 | Delanty et al. | 128/287 |
| 3,912,565 | 10/1975 | Koch et al. | 156/85 |

Primary Examiner—William A. Powell
Assistant Examiner—Jerome W. Massie
Attorney, Agent, or Firm—E. Kelly Linman; Fredrick H. Braun; John V. Gorman

[57] ABSTRACT

In a preferred embodiment, a continuous elastic ribbon is fed to a diaper web assembly station in a stretched condition. While traveling to the assembly station, an adhesive is applied to discrete lengths of the elastic ribbon at regularly spaced intervals. Simultaneously, discrete absorbent core segments as well as webs of moisture-impervious backsheet material and moisture-pervious topsheet material are fed to the diaper web assembly station. At the station, the stretched elastic ribbon is adhered to the moisture-impervious backsheet web in the discrete areas of the elastic which are covered by adhesive at predetermined points along the length of said web. After the adhesive has set up, the assembled web and the elastic contained therein is severed in its unadhered areas, whereupon the unadhered end portions become relaxed and inactive without affecting the functionality of the adhered portions in the ultimate assemblage. The inventive concept in its broadest sense relates to the continuous adherence of discrete lengths of stretched elastic to a continuously moving web at relativey high operating speeds and thereafter severing the elastic in the unadhered areas to produce elasticized structures having discrete strands of elastic adhered thereto at predetermined locations along their length. In a particularly preferred embodiment, the aforementioned process is utilized to apply discrete elastic leg bands to a disposable diaper structure to provide improved containment and fit therein.

27 Claims, 11 Drawing Figures

METHOD AND APPARATUS FOR CONTINUOUSLY ATTACHING DISCRETE, STRETCHED ELASTIC STRANDS TO PREDETERMINED ISOLATED PORTIONS OF DISPOSABLE ABOSRBENT PRODUCTS

BACKGROUND OF THE INVENTION

Method and apparatus for securing an elastic ribbon in stretched condition to a continuously moving web in the manufacture of garments and the like is well known in the art. This may be done either by sewing, by the use of a heat-activated coating on the elastic or by the use of a separate adhesive. It is also known that this process can be carried out in such a way that the elastic is joined in spots, i.e., not continuously secured to the moving web.

U.S. Pat. No. 3,828,367 which issued to Bourgeois on Aug. 13, 1974 is representative of such prior art processes. The patent to Bourgeois is directed to a method for the continuous manufacture of disposable panties. The disclosure of Bourgeois teaches the adherence of a stretched elastic element to a moving web in which the entire length of elastic is attached, said entire length of elastic being functional in the finished articles cut from the web. Bourgeois further suggests that the elastic may be adhered at all points of contact with the fabric web, or alternatively at spaced points along the entire length of elastic.

U.S. Pat. No. 3,560,292 which issued to Butter on Feb. 2, 1971 and which is also typical of the prior art, discloses a non-continuous process for fastening a tensioned elastic band to a textile sheet by fusion bonds or welds at least at the ends of the band and preferably at uniformly spaced spots throughout the entire extent of the band. In the disclosed embodiment, baby pants made of a textile sheet of cellulose or the like have elastic bands secured to the leg opening and waistband portions thereof. During the welding step, the elastic bands are spot welded or fusion bonded at their ends by appropriate tools to the cut-to-size material positioned therebeneath by means of heat and pressure. After the welding spots have cooled off, the preliminary tensioning of the elastic bands is released and the projecting ends of the elastic bands are severed and discarded to facilitate assembly of the garment.

U.S. Pat. No. 3,616,770 which issued to Blyther et al. on Nov. 2, 1971 discloses apparatus for separating garments to which a continuous band of elastic has been sewn along the entire length thereof. In a preferred embodiment, a continuous band of elastic material is fed from a reel under tension and the band and the garments are drawn through the sewing machine by suitable feed means which also serve to maintain the tension in the elastic. A pneumatically operated cutting device positioned immediately after the feed means cuts the elastic band between the garments, thereby separating the elasticated articles.

The prior art completely fails, however, to teach means for continuously joining elastic bands in discrete, spaced areas while in a stretched condition at predetermined points along a continuously moving, substantially inelastic web, said web being thereafter severed in the areas where said elastic is unjoined to said web so that the unadhered areas of the elastic bands become relaxed, inactive, and non-functional.

OBJECTS OF THE INVENTION

Accordingly, it is an object of the present invention to provide method and apparatus for joining continuous bands of stretched elastic in discrete, spaced areas at predetermined points along a continuously moving inelastic web.

It is a further object of the present invention to provide method and apparatus for severing the continuous bands of elastic in their unjoined areas so that the unsecured portions of the elastic become relaxed, inactive and nonfunctional in the finished elasticized articles cut from the web.

It is yet another object of the present invention to provide method and apparatus for the manufacture of disposable absorbent diapers having discrete elastic leg bands secured thereto, said leg bands being functional to gather said diapers only in the areas of securement between said leg bands and said diapers.

It is still a further object of the present invention to secure said discrete elastic bands to a continuously moving web by means of an adhesive that is elastomeric after it becomes set, thereby permitting gathering of the elasticized articles cut from said web and subsequent stretching of the elastic members adhered thereto without any substantial separation therebetween.

SUMMARY OF THE INVENTION

In a particularly preferred embodiment of the present invention, a method is provided for continuously attaching discrete lengths of elastic ribbon to a moving web, said method comprising the steps of: feeding an elastic ribbon to an assembly station in a stretched condition; applying adhesive intermittently to discrete lengths of said continuous elastic ribbon at predetermined intervals while the stretched elastic is being fed to said assembly station; feeding a web of substantially inelastic material to said assembly station; adhering the discrete lengths of stretched elastic ribbon to said web at said assembly station in the discrete areas having adhesive applied thereto; cutting said web and said elastic ribbon transversely in an area where said elastic is not adhered to said web, thereby forming severed unadhered ends of elastic at both ends of each discrete length of stretched elastic ribbon adhered to said web; and allowing the severed unadhered ends of said elastic ribbon to relax and contract to their unstretched state, whereby the presence of the unadhered elastic ends does not interfere with the performance of the web or the discrete length of adhered elastic ribbon. In a particularly preferred embodiment, the adhesive employed to secure the elastic ribbon to the web is elastomeric after it has set up, thereby allowing gathering of the individual articles cut from the web and subsequent stretching of the elastic members adhered thereto without any substantial separation therebetween.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in connection with the accompanying drawings in which:

DETAILED DESCRIPTION OF THE INVENTION

U.S. Pat. No. 3,860,003 which issued to Buell on Jan. 14, 1975, and which is hereby incorporated herein by reference, discloses a number of disposable diaper embodiments employing elastically contractible, flexible side portions to which the method and apparatus of the present invention are particularly well suited. It will be readily apparent to those skilled in the art, however, that although the following description of the present invention is in connection with disposable diaper structures having discrete elastic leg bands secured at predetermined locations along their length, the present invention may be practiced with equal facility and at high speed on any continuously moving web of interconnected articles having discrete elastically contractible bands secured thereto at predetermined locations along their length.

Figures 1, 2, 4:
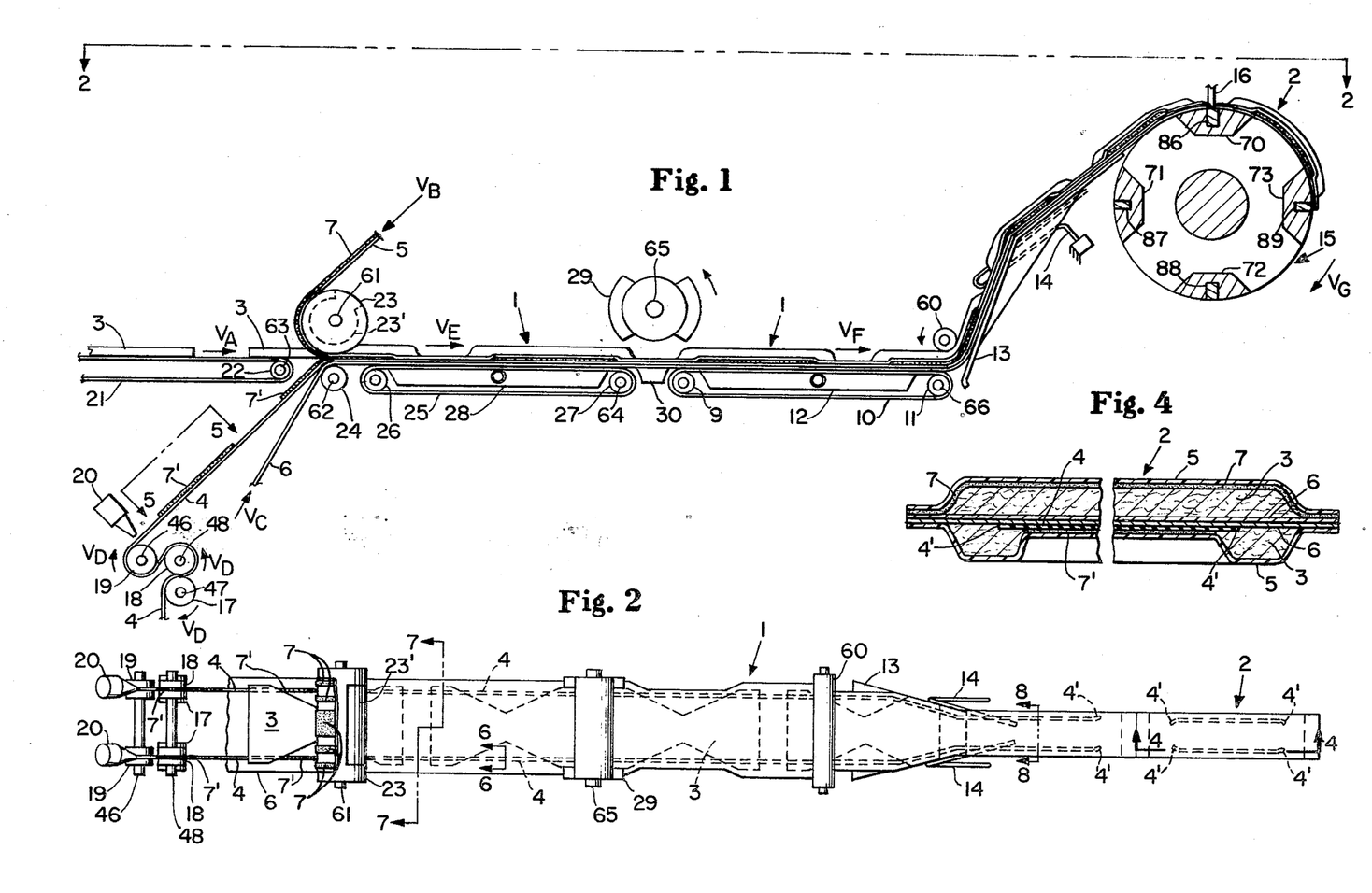
FIG. 1 is a simplified sectional side elevation view showing the assembly of a web of disposable diaper material having stretched elastic bands secured thereto at regularly spaced locations along its length, said web being thereafter C-folded and cut at predetermined points along its length to form individual disposable diapers having discrete elastic leg bands.
FIG. 2 is a simplified plan view of the disposable diaper web illustrated in FIG. 1, taken along view line 2—2 in FIG. 1, illustrating the outline of the discrete absorbent pads, the positioning of the side notches and the location of the continuous, stretched elastic strands in the assembled web throughout web assembly, C-folding and cutting operations.
FIG. 4 is an enlarged, simplified, cross-sectional view of a diaper taken at a point corresponding to that of section line 4—4 of FIG. 2, said diaper being illustrated in a planar condition for purposes of clarity, said view illustrating a preferred relationship between the moisture-impervious backsheet, the moisture-pervious topsheet, the absorbent pad and the stretched elastic leg bands in a diaper which has been severed from the web, but which is still being maintained in tension.

Referring to FIGS. 1 and 2, there is shown a continuous web 1 comprised of a plurality of interconnected disposable diapers 2, each diaper being comprised of an absorbent pad element 3, a pair of continuous, stretched elastic bands 4 secured to the web at predetermined spaced locations, said absorbent pad and said stretched elastic bands being located intermediate a moisture-impervious backsheet 5 and a moisture-pervious topsheet 6. The elastic bands 4 are preferably adhered to the moisture-impervious backsheet 5 intermediate the opposing end portions of the hourglass-shaped absorbent pad elements 3 by means of beads of adhesive 7' applied at predetermined points along the length of the continuous stretched elastic bands 4. This is most clearly illustrated in FIGS. 4 and 6. The components utilized to form the disposable diaper web 1 are maintained in tension throughout the web assembly, C-folding and transverse cutting operations illustrated in FIGS. 1 and 2. Accordingly, the stretched elastic bands 4 are not allowed to gather or pucker the assembled web 1 until tension on the individual diapers 2 cut therefrom has been released.

The web forming or laminating operation is illustrated schematically in FIGS. 1 and 2. The hourglass-shaped absorbent pad segments 3 are fed into the nip between a pair of combining or laminating rolls 23 and 24 at regularly spaced intervals by means of an infeed conveyor 21 operating about discharge roll 22. For purposes of clarity, the pad infeed conveyor 21 and roll 22 are not shown in FIG. 2. In a preferred embodiment, the absorbent pad elements 3 are preferably comprised of airfelt confined within a cellulosic tissue envelope to provide pad integrity in use. A continuous web of moisture-impervious backsheet material 5 is directed about the uppermost combining roll 23, while a continuous web of moisture-pervious topsheet material 6 is directed about the lowermost combining roll 24. As can be seen from FIGS. 2, 4, 7 and 8, the moisture-impervious backsheet material 5 is coated on portions of its innermost surface with a flexible adhesive 7. It should be noted, however, that those portions of the moisture-impervious web 5 which are laterally aligned with the continuous stretched bands of elastic 4 are preferably not coated with adhesive 7 prior to entry into the nip between combining rolls 23 and 24.

In yet another embodiment of the present invention the flexible web laminating adhesive 7 may be applied directly to the moisture-pervious topsheet 6 rather than the moisture-impervious backsheet 5. In the latter embodiment, the flexible adhesive 7 must be applied in such a manner that the moisture-pervious characteristic of the topsheet is not impaired, or the adhesive must be so located that it will not adversely affect the finished structure's ability to absorb body exudates, or both.

The continuous bands of elastic 4 are preferably fed without any residual tension into a low-pressure nip formed between a pair of metering rolls 17 and 18. In a preferred embodiment, the low-pressure nip contacts opposite surfaces of the elastic bands, but exerts only slight pressure thereon to minimize deformation of the bands since deformation of the bands adversely affects the system's ability to match the velocity of the bands to the peripheral velocity of the metering rolls. The continuous bands of elastic 4 are wrapped almost completely about the periphery of metering rolls 18 and are thereafter fed almost completely about the periphery of an additional pair of identical metering rolls 19, as shown in FIGS. 1 and 2. The continuous bands of elastic 4 are thereafter directed into the nip formed between combining rolls 23 and 24 intermediate the web of backsheet material 5, the absorbent pad elements 3 and the web of topsheet material 6. The rolls 17, 18 and 19 act to meter the elastic being fed into the combining nip formed between rolls 23 and 24 at an extremely accurate and predetermined rate. The accurate metering is provided by minimizing slippage of the elastic bands relative to the surface of the metering rolls and by minimizing deformation of the elastic bands. The low-pressure nip formed between rolls 17 and 18 and the relatively large contact area between the elastic bands 4 and the surface of rolls 18 and 19 function well in both regards. Furthermore, the low-pressure nip and the S-wrap arrangement of rolls 17, 18 and 19 minimize deformation of the bands, which would otherwise adversely affect the system's metering accuracy. The S-wrap metering system utilized in a preferred embodiment of the present invention provides a relatively constant resistance on the elastic so that when the peripheral velocity $V_D$ of the metering rolls 17, 18 and 19 is lower than the infeed velocity $V_B$ of the substantially inelastic moisture-impervious backsheet 5 and the infeed velocity $V_C$ of the substantially inelastic moisture-pervious topsheet 6 at the combining nip formed between rolls 23 and 24, the continuous bands of elastic 4 are uniformly stretched and maintained under constant tension along that portion of their length between metering rolls 19 and combining rolls 23 and 24. In yet another embodiment of the present invention, a second low-pressure nip may be formed between metering rolls 18 and metering rolls 19, and the elastic bands may be fed directly about metering rolls 18 into said second nip. The latter arrangement is, however, less preferred due to the tendency of the nip to exert pressure on the elastic bands and cause deformation thereof.

The incoming velocity $V_A$ of the uniformly spaced absorbent pad elements 3 is approximately equal to the incoming velocity $V_B$ of the moisture-impervious backsheet 5 and the incoming velocity $V_C$ of the moisture-pervious topsheet 6. The difference between the surface or peripheral velocity $V_D$ of metering rolls 17, 18 and 19 and the velocity of incoming web 5, incoming web 6 and the incoming pad elements 3 at the nip between the combining rolls 23 and 24 thus determines the amount of draw or stretch in the continuous elastic bands 4.

As is illustrated in FIGS. 1 and 2, a pair of glue applicators 20 is preferably employed to apply a predetermined amount of adhesive 7' at a predetermined spaced intervals along the length of the continuous bands of elastic 4. Because the degree of tension in the continuous elastic bands 4 between the metering rolls 19 and the nip formed between the combining rolls 23 and 24 is uniform, the discrete adhesive beads 7' can be accurately controlled both as to length and spacing so as to precisely align the adhesive 7' with the moisture-impervious backsheet 5 in an area intermediate the opposing end portions of each hourglass-shaped absorbent pad segment 3 at the combining nip between rolls 23 and 24. In yet another embodiment of the present invention, the entire surface of the elastic ribbon could be coated with a heat-activated adhesive prior to the web assembly station, and suitable heating means provided at the assembly station to activate the adhesive only in the desired areas of securement of the web. In still another embodiment of the present invention, a heat-sealable elastic ribbon may be employed, and suitable heating means provided prior to or at the assembly station to raise the surface temperature of the ribbon sufficiently high in the desired areas of securement that the ribbon may be adhered to the web at said areas when it passes through the assembly station. One heat-sealable elastic material from which such a ribbon may be extruded is available from Shell Chemical Company, Polymers Division, of Cleveland, Ohio under the designation Kraton G Thermoplastic Rubber.

Attaching the stretched elastic bands 4 to the moisture-impervious backsheet 5 in the manner described herein eliminates adhesive bleed-through on the wearer contact surfaces of the diaper, particularly in situations wherein the adhesive 7' is subjected to compression, as in the nip between laminating rolls 23 and 24. Since many adhesives exhibit a degree of surface tackiness after set up, thus producing a higher coefficient of friction against the wearer's skin, the prolonged adhesive-to-skin contact which would likely occur due to the presence of the stretched elastic leg bands could result in chafing or rubbing and consequent wearer discomfort if the adhesive 7' were secured to the moisture-pervious topsheet 6 rather than the moisture-impervious backsheet 5. Accordingly, the former embodiment is generally preferred over the latter embodiment in the practice of the present invention. To avoid such wearer discomfort problems, the moisture-pervious topsheet 6 could, however, be precoated prior to securement of the elastic to render it non-porous within the area of elastic/adhesive attachment, thereby permitting joinder of the elastic bands 4 directly to the moisture-pervious topsheet 6 by means of adhesive 7' without creating an adhesive bleed-through problem. In yet another embodiment, a narrow, moisture-impervious film strip could be laminated between the elastic band and the moisture-pervious topsheet.

In a particularly preferred embodiment of the present invention, a fixed-gap clearance is maintained between the uppermost combining roll 23 and the lowermost combining roll 24. In the alternative, a variable-gap nip employing constant force either alone or in combination with a minimum fixed-gap clearance might be employed. The upper-most combining roll 23 preferably has a recessed portion 23' in its outermost surface designed to accept the hourglass-shaped absorbent pad segments 3 so that uniform pressure may be applied to secure the remaining portions of the diaper web together. As is illustrated in the cross-section of FIG. 6, the adhesive 7' applied to the continuous elastic bands 4 is preferably extruded laterally by the action of the combining rolls 23 and 24 so as to produce the maximum feasible contact area between the moisture-impervious backsheet 5 and the elastic bands 4. This is desirable not only from the standpoint of maximizing the degree of securement between the elastic bands 4 and the backsheet 5, but also from the standpoint of minimizing any inhibiting effect that the adhesive might have on the ability of the elastic bands to expand and contract after the adhesive has set up and tension has been removed therefrom.

Figure 6:
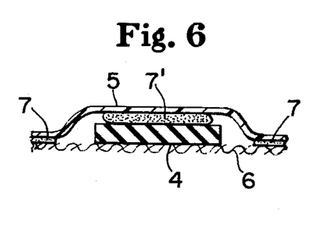
FIG. 6 is an enlarged cross-sectional view taken along section line 6—6 in FIG. 2, illustrating a preferred relationship between the moisture-impervious backsheet, the moisture-pervious topsheet and the adhesive utilized to secure the stretched elastic bands to the backsheet after they have been combined by the laminating rolls.
Figure 7:
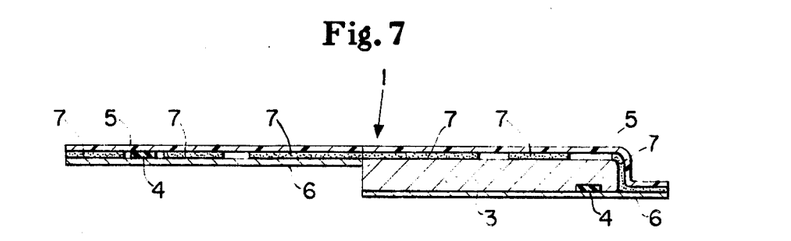
FIG. 7 is an enlarged cross-sectional view taken along section line 7—7 in FIG. 2, illustrating a preferred relationship between the moisture-impervious backsheet, the moisture-pervious topsheet and the stretched elastic bands in those portions of the web where the elastic bands are unsecured to the web.

As is illustrated in FIGS. 2 and 7, the moisture-pervious topsheet 6 is preferably adhered to those portions of the coterminous moisture-impervious backsheet 5 with which it comes in contact by means of any suitable flexible adhesive 7. Those portions of the elastic bands 4 which overlap the absorbent pad elements 3 and interconnect one diaper to another are preferably unsecured to the diaper web 1, as will be described in greater detail hereinafter. It is therefore preferable that no adhesive 7 be provided in the areas of the diaper through which the unsecured portions of the continuous stretched elastic bands 4 pass. Thus, the web of backsheet material 5 is preferably supplied to the combining nip with a striped pattern of adhesive such as is illustrated in FIGS. 2, 6, 7 and 8 applied to its innermost surface. The hourglass-shaped, semi-rigid absorbent pad elements 3 are held relatively immobile with respect to the topsheet 6 and the backsheet 5, since their lowermost surface is adhered directly to the backsheet by means of the stripes of adhesive 7. In addition, they are tightly sandwiched between the topsheet 6 and the backsheet 5 which are adhered to one another about most of the periphery of the pad elements 3.

After passing through the combining nip between rolls 23 and 24, the web is passed onto a perforated vacuum laminating belt 25 operating about rolls 26 and 27, as illustrated in FIG. 1. The vacuum laminating belt 25 is operated at a velocity $V_E$ equal to that of the incoming webs 5 and 6 and the incoming pad elements 3 to maintain uniform tension in the continuous stretched elastic bands 4. Suction is drawn on the web through the perforated belt 25 by means of a suction box 28 located intermediate rolls 26 and 27 just beneath the innermost surface of the perforated conveyor belt. Since the moisture-impervious backsheet 5 is located on the uppermost surface of the web 1, suction applied from the moisture-pervious topsheet side of the web tends to secure the web together until the adhesive 7 securing the various components of the diaper web together and the adhesive 7' securing the stretched elastic bands 4 to the moisture-impervious backsheet 5 have had an opportunity to set up.

From the vacuum laminating belt 25, the assembled diaper web 1 is preferably passed between a rotating trim knife 29 and an anvil table 30 which trims a portion of the excess topsheet and backsheet material from the web in an area adjacent the recessed portions of the hourglass-shaped pad segments 3 to produce a web having the general outline illustrated in FIG. 2. The vacuum laminating belt 25 assists in maintaining proper register of the web 1 and the absorbent pad elements 3 contained therein with respect to the trim knife 29 and anvil table 30 so that the excess material is removed precisely at the desired point. The trim knife 29 and anvil table 30 form no part of the present invention, and, accordingly, may be of any conventional design well known in the art. The excess topsheet and backsheet material severed from the web 1 are preferably removed by vacuum means which are also well known in the art.

From the trim knife 29 and anvil table 30, the continuous web 1 of interconnected disposable diapers 2 is fed onto a perforated vacuum hold-down belt 10 operating about rolls 9 and 11, as illustrated in FIG. 1. Suction is drawn on the web 1 through the perforated belt 10 by means of a suction box 12 located intermediate rolls 9 and 11 just beneath the innermost surface of the perforated conveyor belt. The purpose of the vacuum hold-down belt 10 is to grip the lowermost surface of the web 1 and thereby provide sufficient resistance to slippage so that tension can be applied to those portions of the web located downstream from the vacuum hold-down belt. Since there is essentially no movement between the lowermost surface of the web 1 and the uppermost surface of the vacuum hold-down belt 10, the web travels at substantially the same velocity as the belt, which for purposes of illustration will be referred to hereinafter as $V_F$. In order to maintain the continuous web 1 and the continuous elastic bands 4 contained therein in a stretched condition, the velocity $V_F$ of the vacuum hold-down belt 10 is preferably equal to the velocity $V_E$ of the vacuum laminating belt 25.

Figure 3:
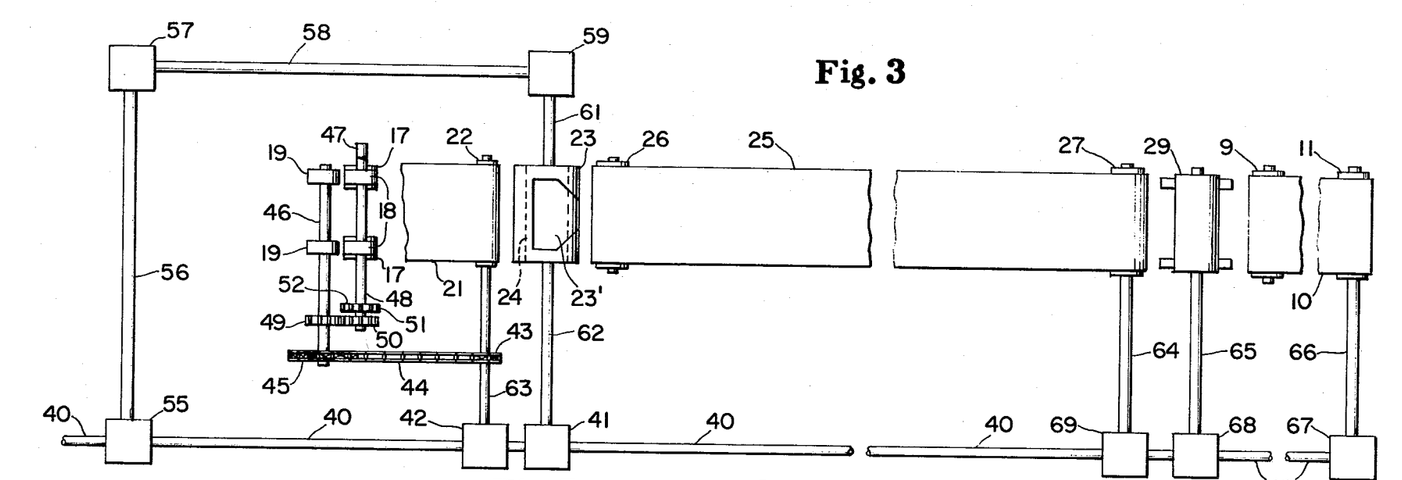
FIG. 3 is a simplified plan view of the assembly station shown in FIGS. 1 and 2, illustrating a preferred drive mechanism for the apparatus.

FIG. 3 is a simplified schematic illustration of a preferred drive system employed to power the web combining rolls 23 and 24, the elastic metering rolls 17, 18 and 19, the pad infeed conveyor belt 21, the vacuum laminating conveyor belt 25, the trim knife 29, and the vacuum hold-down conveyor belt 10. In a preferred embodiment, all of the aforementioned equipment is driven by means of a lineshaft 40. The vacuum hold-down belt 10 is driven by means of a right-angle power take-off 67 which supplies power to the head pulley 11 of the conveyor by means of connecting shaft 66. Another right-angle power take-off 68 is utilized to drive the rotating trim knife 29 by means of connecting shaft 65. Right-angle power take-off 69 which connects to the head pulley 27 of the laminating conveyor belt 25 supplies power thereto by means of connecting shaft 64. The lowermost combining roll 24 is also driven by the lineshaft by means of right-angle power take-off 41 and connecting shaft 62, while the uppermost combining roll 23 is driven in synchronization therewith by means of right-angle power take-off 59 and connecting shaft 61. As is apparent from FIG. 3, right-angle power take-off 59 is connected to the lineshaft 40 by means of right-angle power take-offs 55 and 57 and connecting shafts 56 and 58. Right-angle power take-off 42 is utilized to drive both the pad infeed conveyor 21 rotating about head pulley 22 and the S-wrap metering rolls 17, 18 and 19 utilized to feed the elastic bands 4 to the web laminating station. This is accomplished, in a preferred embodiment of the present invention, by providing a chain drive comprising sprocket 43 secured to shaft 63, sprocket 45 secured to shaft 46 and chain 44 connecting the two sprockets. Metering rolls 19 which are fixedly mounted on shaft 46 are thus driven in synchronization with, but at a lower peripheral velocity than the laminating rolls 23 and 24 by means of the chain drive system described above. Since each of the S-wrap metering rolls 17, 18 and 19 must operate at the same peripheral velocity $V_D$, mating gears 49 and 50 (FIG. 3) mounted on shafts 46 and 48 respectively are preferably utilized to drive the rolls 19 and 18 fixedly mounted thereon, while mating gears 51 and 52 (FIG. 3) mounted on shafts 48 and 47 respectively are preferably utilized to drive the rolls 17 fixedly mounted on shaft 47. The degree of stretch or draw in the elastic bands 4 can thus easily be controlled by altering the drive speed of S-wrap metering rolls 17, 18 and 19 in relation to the speed of the upper and lower combining rolls 23 and 24. In the illustrated embodiment, this is easily accomplished by changing sprocket 43 and/or sprocket 45.

Figure 8:
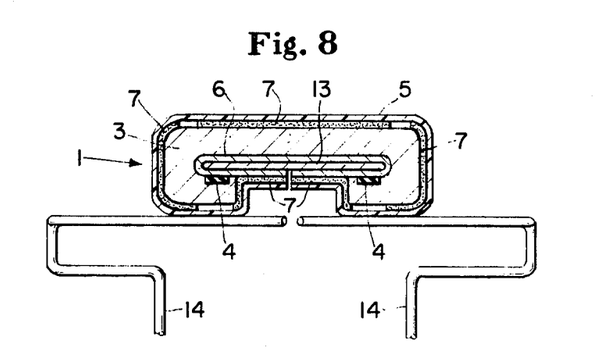
FIG. 8 is an enlarged, simplified, cross-sectional view taken along section line 8—8 of FIG. 2, illustrating the tendency of the web guides to cause the outermost portions of the diaper web to wrap themselves about the board folder located at the infeed to the rotary drum.

After passing over the vacuum hold-down belt 10, the web 1 is preferably directed about idler roll 60 and onto the surface of a conventional board folder 13. As is illustrated in FIG. 2, the board folder 13 tapers from an infeed width substantially equal to the maximum width of the diaper web 1 in its unfolded condition to a discharge width substantially equal to the overall width of the diaper web after C-folding. The lateral edge portions of the diaper web are directed about board folder 13 by means of cooperation between a pair of infeed guiderails 14, as illustrated in FIGS. 1 and 2, and a slight change in direction of the board folder just prior to entrance of the C-folded web onto the surface of a rotary drum 15. The cross-sectional configuration of the web at this particular point is illustrated in FIG. 8.

A particularly preferred means for C-folding the continuous, elasticized diaper web 1 and transversely cutting the discrete disposable diapers 2 from the continuous web while said web and the diapers cut therefrom are maintained in tension is described in greater detail in the copending, commonly-assigned application of Leonard C. Hooper and Gerald M. Weber entitled METHOD AND APPARATUS FOR FOLDING AND CUTTING AN INTERCONNECTED WEB OF DISPOSABLE DIAPERS OR THE LIKE HAVING STRETCHED ELASTIC LEG BANDS SECURED THERETO, Ser. No. 595,477, filed July 11, 1975, said application being hereby incorporated herein by reference. The C-folded diaper web 1 is fed onto the periphery of the rotating drum 15 so that each diaper segment 2 is in register with one of the transverse cutting and transverse folding stations located about the periphery of the drum. The drum 15, as explained in detail in the aforementioned application of Hooper and Weber, preferably has a peripheral velocity $V_G$ slightly greater than the incoming velocity $V_F$ of the continuous web 1. The drum preferably has four diaper cutting and transverse folding stations, shown generally at 70, 71, 72 and 73, equally spaced about its periphery. The web 1 and the individual diapers 2 cut therefrom are preferably secured to the periphery of the drum by means of spring-loaded gripping elements which compensate for the difference in the velocity $V_G$ of the rotary drum 15 and the infeed velocity $V_F$ of the web 1, said spring-loaded gripping elements functioning to maintain both the web and the individual diapers cut therefrom in tension until completion of the transverse folding operation of the individual diapers, which occurs downstream of the transverse cutting station. In preferred embodiment, the individual diapers 2 are cut from the web 1 at a predetermined point intermediate the absorbent pad elements 3 by the interaction of a rotary knife having one or more blades secured to its periphery, i.e., blade 16 in FIG. 1, and one of the cutting anvils 86, 87, 88 or 89 associated with each of the diaper handling stations on the periphery of the drum.

FIGS. 1 and 2 illustrate the condition of the web 1 and an individual diaper 2 at the instant the transverse cut has been effected. As can be seen from FIGS. 2 and 4, the unsecured portions 4' of the elastic bands 4 which are not adhered to the backsheet 5 by means of adhesive 7' are non-functional after the individual diapers 2 have been severed from the web 1. Accordingly, when the individual diapers 2 are cut from the web 1, the non-functional portions 4' of the elastic bands 4 are allowed to relax and retract to their free length without inhibiting the functioning of those portions of the bands which are adhered to the backsheet 5 by means of adhesive 7'.

Thus, applicant has provided method and apparatus for continuously forming articles having discrete stretched bands of elastic adhered at predetermined locations along their length, said method preferably comprising: feeding an elastic ribbon to an assembly station in a stretched condition; applying adhesive intermittently on said elastic ribbon at predetermined intervals while the elastic is being fed to said assembly station; feeding first and second webs of inelastic material to said assembly station; adhering the stretched elastic ribbon to said first web at said assembly station in those areas of the ribbon that have adhesive applied thereto; applying adhesive to said second web while said second web is being fed to said assembly station so that said adhesive areas will lie on either side of the elastic ribbon adhered to said first web; adhering said second web to said first web at said assembly station, thereby forming a channel for said elastic ribbon; cutting said webs transversely along a line severing said elastic ribbon in a portion of its length which is not adhered to said first web; and allowing the severed unadhered ends of said elastic ribbon to relax and contract to their unstretched length within said channel, whereby the presence of the unadhered ends does not interfere with the performance of either the web or the adhered elastic ribbon after converting the assemblage into a discrete elasticized article.

Figure 5:
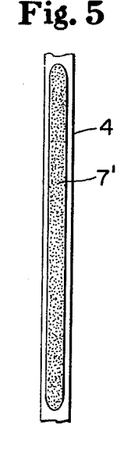
FIG. 5 is an enlarged view taken along view line 5—5 in FIG. 1, illustrating a preferred adhesive pattern applied to the stretched strands of elastic.
Figure 9:
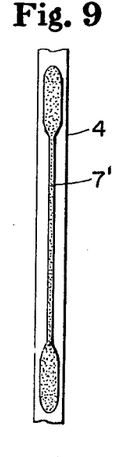
FIGS. 9 - 11 are views similar to that of FIG. 5, illustrating alternative adhesive patterns which may be employed in the practice of the present invention.
Figure 10:
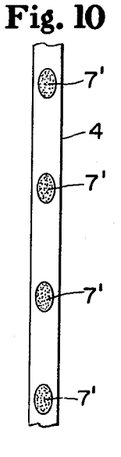
Figure 11:
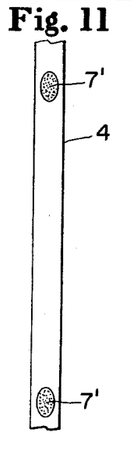

FIG. 6, which is a cross-sectional view taken along section line 6—6 of FIG. 2, illustrates a preferred condition of the adhesive 7' after the web has passed between the combining rolls 23 and 24. It is desirable in the practice of the present invention to compress the bead of adhesive 7' to the extent feasible so as to maximize the contact area between the backsheet 5 and the elastic band 4. A thin layer of adhesive is also generally preferable to a thicker layer of adhesive due to the fact that it has a lesser tendency to inhibit the gathering and stretch characteristics of the elastic bands 4 in their areas of adherence to the web. FIG. 5 is illustrative of one preferred adhesive application pattern prior to assembly of the laminated web. FIGS. 9 – 11 are representative of alternative preferred embodiments of adhesive patterns which may be employed in the practice of the present invention. The embodiment of FIG. 9 is particularly desirable when it is desired to uniformly gather the elasticized article throughout the area of adherence between the elastic bands 4 and the backsheet 5. The reduced amount of adhesive applied in the centermost areas of the elastic bands 4 has a lesser tendency to restrict expansion or contraction of the elastic, while the greater quantities of adhesive at the end points act to firmly secure the elastic bands 4 to the backsheet 5. The embodiment of FIG. 10 may be employed in situations where the adhesive 7' is not particularly flexible after set up, yet it is desirable to gather the elasticized article with at least some degree of uniformity along the elasticized portions thereof. FIG. 11, on the other hand, is illustrative of an embodiment wherein uniform gathering of the elasticized article along the elasticized portions thereof is not critical. If desired, the adhesive 7' may, of course, be applied to opposite surfaces of the stretched elastic bands 4 to facilitate securing them to both the backsheet 5 and the topsheet 6.

In a particularly preferred embodiment of the present invention, the adhesive 7' used for adhering portions of the stretched elastic members 4 to the moisture-impervious backsheet 5 is comprised of a hot-melt adhesive which is so formulated that it is elastomeric after it has set up. This allows essentially uninhibited gathering of the diaper side flaps and subsequent stretching of the elastic members adhered thereto without any substantial separation therebetween. As should be apparent from the foregoing, the adhesive 7' utilized in the practice of the present invention must set up prior to the time at which tension is released in the non-functional end portions 4' of the elastic bands 4. The use of a hot-melt adhesive in a preferred embodiment of the present invention permits utilization of high speed product manufacturing techniques without introducing the inherent speed limitations or complexity of more traditional elastic attaching methods such as sewing, conventional adhesives, etc. One stretchable elastomeric hot-melt adhesive which has been found particularly suitable for use in the practice of the present invention is a high viscosity, ethylene vinyl acetate based material available from Findley Adhesives, Inc., of Milwaukee, Wis. under Formula No. 619-336-20. However, any fast setting adhesive having the desired elastomeric and adhesion properties upon set up could be utilized with equal facility.

Thus, it is apparent that there has been provided, in accordance with the present invention, method and apparatus for intermittently attaching a continuous, stretched elastic ribbon to a continuously moving web at discrete, predetermined locations along the length of said web, and thereafter severing said elastic ribbon in a portion of its length which is not adhered to the web so that the severed unadhered ends of the elastic ribbon are allowed to relax and become non-functional. It should be noted, however, that while the invention has been described in conjunction with specific preferred embodiments thereof, it is evident that many alternatives, modifications and variations will be apparent to those skilled in the art in light of the foregoing description. Accordingly, it is intended to embrace all such alternatives, modifications, and variations that fall within the spirit and broad scope of the appended claims.

What is claimed is:

1. A method for continuously attaching discrete lengths of elastic ribbon to isolated portions of a moving, substantially inelastic web of interconnected articles to impart an elasticized character to predetermined, isolated portions of said articles while preserving the substantially inelastic character of said articles in areas where said ribbon is unattached to said web, said method comprising the steps of:
   (a) feeding an elastic ribbon to an assembly station in a stretched condition;
   (b) applying adhesive intermittently to discrete lengths of said stretched elastic ribbon at predetermined intervals along the length of said ribbon while said stretched elastic ribbon is being fed to said assembly station;
   (c) feeding a web of interconnected articles comprised of a substantially inelastic material to said assembly station;
   (d) adhering the discrete lengths of stretched elastic ribbon to predetermined, isolated portions of the articles comprising said web at said assembly station in the discrete areas of said elastic ribbon having adhesive applied thereto;
   (e) maintaining said elastic ribbon in a stretched condition at least until said adhesive sets up;
   (f) cutting said elastic ribbon transversely in an area which is not adhered to said web, thereby forming severed, unadhered ends of elastic at both ends of each discrete length of stretched elastic ribbon adhered to said web; and
   (g) allowing the severed, unadhered ends of said elastic ribbon to relax and contract to their unstretched state, whereby said unadhered ends do not impart an elasticized character to said web nor do they interfere with the functioning of the elasticized portions of the web to which said discrete lengths of elastic ribbon are adhered.

2. The method of claim 1, wherein said articles and said elastic ribbon are simultaneously cut from said web at a predetermined point along the length of said web in an area in which said elastic ribbon is not adhered to said web while said web and said elastic ribbon are maintained in a stretched condition, thereby forming discrete elasticized articles having discrete elastic ribbons adhered thereto along a portion of their length.

3. The method of claim 1, wherein said adhesive is intermittently applied to said elastic ribbon in continuous beads.

4. The method of claim 3, wherein said adhesive is intermittently applied to said elastic ribbon in continuous beads having greater mass at their end points.

5. The method of claim 1, wherein said adhesive is intermittently applied to said elastic ribbon in the shape of discrete dots in the desired areas of adhesion between said ribbon and said web.

6. The method of claim 1, wherein said adhesive becomes elastomeric after set up to permit expansion and contraction of said web and the secured portions of said elastic ribbon without any substantial separation therebetween.

7. The method of claim 6, wherein said stretched elastic ribbon is adhered to said web by means of a hot melt adhesive.

8. The method of claim 1, wherein said discrete lengths of elastic ribbon are adhered to said web in the discrete areas having adhesive applied thereto by passing said web and said ribbon into the nip formed between a pair of combining rolls which exert pressure thereon, said pressure acting to extrude said adhesive and thereby minimize its thickness and maximize the area of contact between said adhesive, said elastic ribbon and said web.

9. A method for continuously attaching discrete lengths of elastic ribbon to isolated portions of a moving, substantially inelastic web of interconnected articles, to impart an elasticized character to predetermined, isolated portions of said articles while preserving the substantially inelastic character of said articles in areas where said ribbon is unattached to said web, said method comprising the steps of:
   (a) feeding an elastic ribbon having a heatactivated adhesive coating on at least one surface thereof to an assembly station in a stretched condition;
   (b) feeding a web of interconnected articles comprised of a substantially inelastic material to said assembly station;
   (c) adhering discrete lengths of said stretched elastic ribbon to predetermined isolated portions of the articles comprising said web at said assembly station by activating said adhesive only in predetermined areas along the length of said elastic ribbon;
   (d) maintaining said elastic ribbon in a stretched condition at least until said adhesive sets up;
   (e) cutting said elastic ribbon transversely in an area which is not adhered to said web, thereby forming severed, unadhered ends of elastic at both ends of each discrete length of stretched elastic ribbon adhered to said web; and
   (f) allowing the severed, unadhered ends of said elastic ribbon to relax and contract to their unstretched state, whereby said unadhered ends do not impart an elasticized character to said web nor do they interfere with the functioning of the elasticized portions of the web to which said discrete lengths of elastic ribbon are adhered.

10. A method of intermittently attaching an elastic ribbon to predetermined, isolated portions of at least one of a pair of continuously moving, substantially inelastic, superposed webs to impart an elasticized character thereto while preserving the substantially inelastic character thereof in areas where said ribbon is unattached to said web, said method comprising the steps of:

(a) feeding an elastic ribbon to an assembly station in a stretched condition;

(b) applying adhesive intermittently on said stretched elastic ribbon at predetermined intervals along the length of said ribbon while said stretched elastic ribbon is being fed to said assembly station;

(c) feeding first and second webs of substantially inelastic material to said assembly station;

(d) adhering the stretched elastic ribbon to predetermined, isolated portions of at least one of said webs at said assembly station in those discrete areas of the ribbon that have adhesive applied thereto;

(e) applying bands of adhesive to at least one of said webs while said webs are being fed to said assembly station, said bands being registered such that they will ultimately lie outside the area occupied by said stretched elastic ribbon;

(f) adhering said second web to said first web at said assembly station in the areas of said bands of adhesive;

(g) maintaining said elastic ribbon in a stretched condition at least until said adhesive on said ribbon sets up;

(h) cutting said webs into discrete articles transversely along a line severing said elastic ribbon in a portion of its length which is not adhered to either of said webs; and (i) allowing the severed, unadhered ends of said elastic ribbon to relax and contract to their unstretched length, whereby said unadhered ends do not impart an elasticized character to the articles cut from said webs nor do they interfere with the functioning of the elasticized portions of said articles to which said elastic ribbon is adhered.

11. The method of claim 10, wherein said substantially inelastic superposed webs and the stretched elastic ribbon secured thereto at spaced locations along its length are maintained in tension at least until said discrete elasticized articles are severed therefrom.

12. A method for continuously attaching discrete lengths of elastic ribbon to predetermined, isolated portions of a moving, substantially inelastic web to impart an elasticized character thereto while preserving the substantially inelastic character thereof in areas where said ribbon is unattached to said web, said method comprising the steps of:

(a) feeding a heat-sealable elastic ribbon to an assembly station in a stretched condition;

(b) feeding a web of substantially inelastic material to said assembly station;

(c) adhering discrete lengths of said heat-sealable elastic ribbon to predetermined, isolated portions of said web at said assembly station by elevating the surface temperature of said ribbon only in predetermined areas along the length of said elastic ribbon;

(d) maintaining said elastic ribbon in a stretched condition until the termperature of said ribbon has been lowered sufficiently to bond said ribbon to said web;

(e) cutting said elastic ribbon transversely in an area which is not adhered to said web, thereby forming severed, unadhered ends of elastic at both ends of each discrete length of stretched elastic ribbon adhered to said web; and (f) allowing the severed, unadhered ends of said elastic ribbon to relax and contract to their unstretched state, whereby the unadhered ends do not impart an elasticized character to said web nor do they interfere with the functioning of the elasticized portions of said web to which said discrete lengths of elastic ribbon are adhered.

13. A method of intermittently attaching a pair of elastic ribbons intermediate the opposed waistband portions of the absorbent pad elements contained in a continuously moving, substantially inelastic web of interconnected disposable diapers to form a pair of discrete elasticized legbands in each of said diapers cut from said web, the waistband portions of said diapers being non-elasticized to provide improved wearer comfort and fit as well as to facilitate securement thereof about the wearer's waist, said method comprising the steps of:

(a) feeding a pair of elastic ribbons to an assembly station in a stretched condition;

(b) applying adhesive intermittently on said stretched elastic ribbons at predetermined intervals along the length of said ribbons while said stretched elastic ribbons are being fed to said assembly station;

(c) feeding first and second webs of substantially inelastic material to said assembly station;

(d) feeding absorbent pad elements having opposed waistband portions intermediate said first and said second webs;

(e) adhering said stretched elastic ribbons to at least one of said webs at discrete locations intermediate the opposed waistband portions of said absorbent pad elements at said assembly station in those discrete areas of the ribbons that have adhesive applied thereto;

(f) applying bands to adhesive to at least one of said webs while said webs are being fed to said assembly station, said bands being registered such that they will ultimately lie outside the area occupied by said stretched elastic ribbons;

(g) adhering said second web, said absorbent pad elements and said first web in superposed relation at said assembly station in the areas of said bands of adhesive;

(h) maintaining said elastic ribbons in a stretched condition at least until said adhesive on said ribbons sets up;

(i) cutting said webs transversely into discrete disposable diapers along a line severing said elastic ribbons in a portion of their length which is not adhered to either of said webs; and (j) allowing the severed, unadhered ends of said elastic ribbons to relax and contract to their unstretched length, whereby said unadhered ends do not impart an elasticized character to the waistband portions of said disposable diapers nor do they interfere with the functioning of the elasticized legband portions of said diapers to which said discrete lengths of elastic ribbon are adhered.

14. The method of claim 13, wherein said first web is comprised of moisture-impervious backsheet material and said second web is comprised of moisture-pervious topsheet material, said method including the step of continuously feeding discrete, hourglass-shaped absorbent pad elements intermediate said first and said second webs at predetermined points along the length of said webs, said elastic ribbons being adhered to said first web at points intermediate the opposed end portions of each of said hourglass-shaped absorbent pad elements to form a pair of discrete elasticized legbands in each of the discrete disposable diapers cut from said web.

15. The method of claim 14, wherein said stretched elastic ribbons are adhered to said web by means of a hotmelt adhesive which becomes elastomeric after set up, thereby permitting expansion and contraction of said web and the secured portions of said elastic ribbons without any substantial separation therebetween.

16. The method of claim 14, wherein said first and second webs, said absorbent elements, and said elastic ribbons are formed into a unitary elasticized assemblage by simultaneously passing them into a nip formed between a pair of combining rolls which exert pressure thereon to bring said elements into intimate contact with each other in the areas where adhesive is present, the moisture-pervious topsheet surface of said assemblage being thereafter subject to suction to secure the entire assemblage together until the adhesive employed to adhere said elastic ribbon has set up.

17. A method of intermittently attaching an elastic ribbon to predetermined, isolated portions of at least one of a pair of continuously moving, substantially inelastic, superposed webs to impart an elasticized character thereto while preserving the substantially inelastic character thereof in areas where said ribbon is unattached to said web, said method comprising the steps of:
(a) feeding an elastic ribbon to an assembly station in a uniformly stretched condition by feeding said ribbon in an unstretched state into a first lowpressure nip formed between a first metering roll and a second metering roll, passing said ribbon partially about the periphery of said second metering roll directly to a third metering roll, passing said ribbon partially about the periphery of said third metering roll, and thereafter feeding said ribbon from said third metering roll to said assembly station by operating said metering rolls at a uniform peripheral velocity less than that of the incoming webs at said assembly station;
(b) applying adhesive intermittently on said stretched elastic ribbon at predetermined intervals along the length of said ribbon while said stretched elastic ribbon is being fed to said assembly station;
(c) feeding first and second webs of substantially inelastic material to said assembly station;
(d) adhering the stretched elastic ribbon to predetermined, isolated portions of at least one of said webs at said assembly station in those discrete areas of the ribbon that have adhesive applied thereto;
(e) applying bands of adhesive to at least one of said webs while said webs are being fed to said assembly station, said bands being registered such that they will ultimately lie outside the area occupied by said stretched elastic ribbon;
(f) adhering said second web to said first web at said assembly station in the areas of said bands of adhesive;
(g) maintaining said elastic ribbon in a stretched condition at least until said adhesive on said ribbon sets up;
(h) cutting said webs into discrete articles transversely along a line severing said elastic ribbon in a portion of its length which is not adhered to either of said webs; and
(i) allowing the severed, unadhered ends of said elastic ribbon to relax and contract to their unstretched length, whereby said unadhered ends do not impart an elasticized character to the articles cut from said webs nor do they interfere with the functioning of the elasticized portions of said articles to which said elastic ribbon is adhered.

18. A method of intermittently attaching an elastic ribbon to predetermined, isolated portions of at least one of a pair of continuously moving, substantially inelastic, superposed webs to impart an elasticized character thereto while preserving the substantially inelastic character thereof in areas where said ribbon is unattached to said web, said method comprising the steps of:
(a) feeding an elastic ribbon to an assembly station in a uniformly stretched condition by feeding said ribbon in an unstretched state into a first lowpressure nip formed between a first metering roll and a second metering roll, passing said ribbon partially about said second metering roll directly into a second low-pressure nip formed between said second metering roll and a third metering roll, and thereafter feeding said ribbon from said second nip to said assembly station by operating said metering rolls at a uniform peripheral velocity less than that of the incoming webs at said assembly station;
(b) applying adhesive intermittently on said stretched elastic ribbon at predetermined intervals along the length of said ribbon while said stretched elastic ribbon is being fed to said assembly station;
(c) feeding first and second webs of substantially inelastic material to said assembly station;
(d) adhering the stretched elastic ribbon to predetermined, isolated portions of at least one of said webs at said assembly station in those discrete areas of the ribbon that have adhesive applied thereto;
(e) applying bands of adhesive to at least one of said webs while said webs are being fed to said assembly station, said bands being registered such that they will ultimately lie outside the area occupied by said stretched elastic ribbon;
(f) adhering said second web to said first web at said assembly station in the areas of said bands of adhesive;
(g) maintaining said elastic ribbon in a stretched condition at least until said adhesive on said ribbon sets up;
(h) cutting said webs into discrete articles transversely along a line severing said elastic ribbon in a portion of its length which is not adhered to either of said webs; and
(i) allowing the severed, unadhered ends of said elastic ribbon to relax and contract to their unstretched length, whereby said unadhered ends do not impart an elasticized character to the articles cut from said webs nor do they interfere with the functioning of the elasticized portions of said articles to which said elastic ribbon is adhered.

19. An apparatus for continuously attaching discrete lengths of elastic ribbon to predetermined, isolated portions of a moving, substantially inelastic web to impart an elasticized character thereto while preserving the substantially inelastic character of said web in areas where said ribbon is unattached to said web, said apparatus comprising:
(a) means for feeding an elastic ribbon to an assembly station in a stretched condition;
(b) means for applying adhesive intermittently to discrete lengths of said elastic ribbon at predetermined intervals along the length of said ribbon while said stretched elastic ribbon is being fed to said assembly station;

(c) means for feeding a web of substantially inelastic material to said assembly station;

(d) means for adhering said discrete lengths of stretched elastic ribbon to predetermined, isolated portions of said web at said assembly station in the discrete areas of said stretched elastic ribbon having adhesive applied thereto;

(e) means for maintaining said elastic ribbon in a stretched condition at least until said adhesive sets up;

(f) means for cutting said elastic ribbon transversely in an area which is not adhered to said web, thereby forming severed, unadhered ends of elastic at both ends of each discrete length of stretched elastic ribbon adhered to said web.

20. The apparatus of claim 19, wherein said means for feeding said elastic ribbon to said assembly station in a stretched condition is comprised of a low-pressure nip formed between first and second metering rolls and a third metering roll independent of said first and second metering rolls, said elastic ribbon being passed into said nip in an unstretched state, partially about the periphery of said second metering roll directly to said third metering roll, partially about said third metering roll, and from said third metering roll to said assembly station, said metering rolls being operated at a uniform peripheral velocity less than that of the incoming webs at said assembly station.

21. The apparatus of claim 19, wherein said means for feeding said elastic ribbon to said assembly station in a stretched condition is comprised of a first low-pressure nip formed between a first metering roll and a second metering roll and a second low-pressure nip formed between said second metering roll and a third metering roll, said elastic ribbon being passed into said first nip in an unstretched state, partially about the periphery of said second metering roll directly into said second low-pressure nip, and from said second nip to said assembly station, said metering rolls being operated at a uniform peripheral velocity less than that of the incoming webs at said assembly station.

22. The apparatus of claim 19, wherein said means for adhering said discrete lengths of stretched elastic to said web at said assembly station in the discrete areas having adhesive applied thereto is comprised of a nip formed between a pair of combining rolls.

23. The apparatus of claim 22, wherein said nip has a fixed gap clearance small enough to apply pressure to said web, said elastic ribbon, and the adhesive joining said ribbon to said web as they pass therethrough.

24. The apparatus of claim 22, wherein said nip has a variable-gap clearance, and a constant force is applied thereto as said web, said elastic ribbon, and the adhesive joining said ribboon to said web pass therethrough.

25. The apparatus of claim 19, wherein said means for cutting said elastic ribbon transversely in an area which is not adhered to said web functions to simultaneously cut discrete articles from said web at a predetermined point along the length of said web.

26. An apparatus for continuously attaching discrete lengths of elastic ribbon to predetermined, isolated portions of a moving, substantially inelastic web to impart an elasticized character thereto while preserving the substantially inelastic character of said web in areas where said ribbon is unattached to said web, said apparatus comprising:

(a) means for feeding an elastic ribbon having a heat-activated adhesive coating on at least one surface thereof to an assembly station in a stretched condition;

(b) means for feeding a web of substantially inelastic material to said assembly station;

(c) means for activating said adhesive coating only at predetermined areas along the length of said elastic ribbon to adhere discrete lengths of said stretched elastic ribbon to predetermined, isolated portions of said web at said assembly station;

(d) means for maintaining said elastic ribbon in a stretched condition at least until said heatactivated adhesive sets up; and (e) means for cutting said elastic ribbon transversely in an area which is not adhered to said web, thereby forming severed, unadhered ends of elastic at both ends of each discrete length of stretched elastic ribbon adhered to said web.

27. An apparatus for continuously attaching discrete lengths of elastic ribbon to predetermined, isolated portions of a moving, substantially inelastic web to impart an elasticized character thereto while preserving the substantially inelastic character of said web in areas where said ribbon is unattached to said web, said apparatus comprising:

(a) means for feeding a heat-sealable elastic ribbon to an assembly station in a stretched condition;

(b) means for feeding a web of substantially inelastic material to said assembly station;

(c) means for adhering discrete lengths of said heat-sealable elastic ribbon to predetermined, isolated portions of said web at said assembly station by elevating the surface temperature of said ribbon only in predetermined areas along the length of said ribbon;

(d) means for maintaining said heat-sealable elastic ribbon in a stretched condition until the temperature of said ribbon has been lowered sufficiently to bond said ribbon to said web; and (e) means for cutting said elastic ribbon transversely in an area which is not adhered to said web, thereby forming severed, unadhered ends of elastic at both ends of each discrete length of stretched elastic ribbon adhered to said web.

* * * * *

UNITED STATES PATENT AND TRADEMARK OFFICE
CERTIFICATE OF CORRECTION

PATENT NO. : 4,081,301
DATED : March 28, 1978
INVENTOR(S) : Kenneth B. Buell

It is certified that error appears in the above—identified patent and that said Letters Patent are hereby corrected as shown below:

Title Page, line 5 of the title, "ABOSRBENT" should read -- ABSORBENT --.

Title Page, under References Cited, line 11, "Burgeois" should read -- Bourgeois --.

Title Page, under References Cited, insert --
| | | | |
|---|---|---|---|
| 3,431,562 | 3/1969 | Souders | 2/221 |
| 3,417,751 | 12/1968 | Murdoch | 128/287 |
| 2,976,199 | 3/1961 | Rand | 154/85 |
| 2,844,502 | 7/1958 | Paxton | 154/139 |
| 2,823,156 | 2/1958 | Hedges | 154/46 |
| 2,820,733 | 1/1958 | Sorel | 154/118 |
| 2,706,699 | 4/1955 | Plansoen et al | 154/140 |
| 1,882,642 | 10/1932 | Jung, Jr | |

--.

Title Page, line 22 of the Abstract, "relativey" should read -- relatively --.

Column 1, line 6, "ABOSRBENT" should read -- ABSORBENT --.

Column 5, line 47, delete "a".

Column 6, line 51, "maximinizing" should read -- maximizing --.

Column 9, line 13, after "1975," insert -- and issued on May 10, 1977 as U.S. Patent 4,022,456, -- and after "application" insert -- and said patent --.

UNITED STATES PATENT AND TRADEMARK OFFICE
CERTIFICATE OF CORRECTION

PATENT NO. : 4,081,301
DATED : March 28, 1978
INVENTOR(S) : Kenneth B. Buell

It is certified that error appears in the above-identified patent and that said Letters Patent are hereby corrected as shown below:

Column 11, line 4, "619-336-20" should read -- 691-336-20 --.

Column 12, line 39, "heatactivated" should read -- heat-activated --.

Column 14, line 35, "to", first occurrence, should read -- of --.

Column 15, line 29, "lowpres-" should read -- low-pres- --.

Column 16, line 13, "lowpres-" should read -- low-pres- --.

Column 17, line 54, "ribboon" should read -- ribbon --.

Column 18, line 23, "heatactivated" should read -- heat-activated --.

Signed and Sealed this

Tenth Day of October 1978

[SEAL]

Attest:

RUTH C. MASON
*Attesting Officer*

DONALD W. BANNER
*Commissioner of Patents and Trademarks*